United States Patent [19]

Stull

[11] 4,115,098

[45] Sep. 19, 1978

[54] PEST CONTROL COMPOSITION AND METHOD

[75] Inventor: Emerson B. Stull, San Antonio, Tex.

[73] Assignee: Stull Chemical Company, San Antonio, Tex.

[21] Appl. No.: 800,423

[22] Filed: May 25, 1977

[51] Int. Cl.$^2$ .......................... A01N 9/36; A01N 9/22; A01N 17/00; A01N 17/10
[52] U.S. Cl. ............................................. 71/93; 71/71; 71/92; 71/94; 71/100; 71/117; 71/121; 71/31; 71/32; 71/DIG. 1; 71/64 C; 424/93; 424/218; 424/249; 424/273 R; 424/286; 424/300; 424/315; 424/326
[58] Field of Search ............... 71/DIG. 1, 93, 71, 117, 71/64; 424/218, 326

[56] References Cited

U.S. PATENT DOCUMENTS

| 3,479,176 | 11/1969 | Wilson | 71/94 |
|---|---|---|---|
| 3,734,867 | 5/1973 | Will | 71/DIG. 1 |
| 3,764,293 | 10/1973 | Guth | 71/DIG. 1 |
| 3,776,857 | 12/1973 | Lindner | 71/DIG. 1 |

*Primary Examiner*—Joseph Paul Brust
*Attorney, Agent, or Firm*—Sigalos & Levine

[57] ABSTRACT

The present invention relates to a pest control composition comprising an aqueous phase having suspended therein substantially uniform droplets of an invert emulsion comprising an external oil system, an internal system comprising water or an oil-in-water emulsion, and at least one pest control agent present in an amount sufficient to control pests, said agent being contained in at least one of said external or internal systems and the method of controlling pests comprising applying said composition to the locus of said pest infestations.

12 Claims, No Drawings

PEST CONTROL COMPOSITION AND METHOD

BACKGROUND OF THE INVENTION

Invert emulsions have been known for many years as sprays for controlling pests. Such emulsions are water-in-oil emulsions and are considered superior to conventional oil-in-water or solution sprays because of reduced drift, evaporation and volatilization of the sprays, particularly during aerial application, increased rain resistance, and improved penetration in the case of systemic pesticides.

An improved invert composition for pest treatment is disclosed in U.S. Pat. No. 3,479,176 and is a marked improvement over the prior art invert emulsions with respect to reduced drift, increased rain resistance and improved penetration. Such invert emulsions are commercially available under the trademark "BIVERT" and consist of an emulsifiable concentrate containing an oil such as petroleum distillate and fatty amine salts and fatty acids, but no pest control agent.

All such invert emulsions, however, do suffer from two major disadvantages; namely, too high a viscosity and droplets that are too large in size. The result is difficulty in utilizing such viscous emulsions with conventional spray equipment and in the case of large size droplets, large volumes are required to cover the pest infested target area. With the application of large volumes of pesticides applied to foliage, damage can be caused due to the toxic effect on the foliage by over-concentration of the emulsifiers and/or oil in the large droplets applied.

These and other problems of present invert emulsions are discussed in detail in a U.S.D.A. Forest Service General Technical report PNW-3 of 1973 entitled "Aerial Spray Adjuvants for Herbicidal Drift Control" by Gratkowski and Stewart.

SUMMARY OF THE INVENTION

The disadvantages of the prior art have been overcome by pest control compositions having droplets of substantially uniform small size and a viscosity such that they flow like water, making them much more suitable for use.

Briefly stated, the present invention comprises a pest control composition comprising an aqueous phase having suspended therein substantially uniform droplets of an invert emulsion comprising an external oil system, an internal phase comprising water or an oil-in-water emulsion, and at least one pest control agent present in an amount sufficient to control pests, said agent being contained in at least one of said external or internal phases.

The invention also comprises the method of controlling pests comprising applying said composition to the locus of said pest infestation.

DETAILED DESCRIPTION

As used herein, the term "pest" is meant to include undesired vegetation, insects, fungi, nematodes, bacteria, and like which it is desired to destroy or control primarily in agricultural activities. For such purpose, there are a wide variety of herbicides, fungicides, bactericides, and insecticides that can be utilized. Often combinations of these biocides are used to control the undesired pest. Examples of biocides are:

| | |
|---|---|
| TREFLAN: | a, 1,1-Trifluoro-2,6-dinitro-N,N-dipropyl-p-toluidine; |
| MILOGARD: | 2-Chloro-4,6-bis(isopropylamino)-s-triazine; |
| PARAQUAT: | 1,1'-Dimethyl-4,4'-bipyridinium ion -- usually present as the dichloride salt or the di(methylsulfate) salt; |
| DEF: | S, S, S-Tributylphosphorotrithioate; |
| GUTHION: | O, O-Dimethyl S-[(4-oxo-1,2,3-benzotriazin-3(4H)-yl)methyl] phosphorodithioate; |
| DIPEL: | Bacillus Thuringiensis; |
| SUTAN: | S-Ethyl diisobutylthiocarbamate; |
| AATREX: | 2-Chloro-4-(ethylamino)-6-(isopropylamino)-s-triazine; |
| KOCIDE: | Cupric hydroxide. |
| BAYFOLAN: | 15% nitrogen, 10% phosphoric acid, 5% potash; |
| NUDRIN: | S-Methyl-N-[(methylcarbamoyl)oxy] thioacetimidate; |
| MANZATE 200: | Manganese ethylene bisdithiocarbamate; |
| BENLATE: | Methyl-1-(butylcarbamoyl)-2-benzimidazolecarbamate; |
| 2,4-D: | 2,4-Dichlorophenoxyacetic acid. |

Application is most effectively made by means of sprays.

In accordance with the present invention, any of the known biocides can be used and they are included in the herein compositions in their usual amounts. As noted, combinations of the biocides can be used if desired. Moreover, with the present invention and, as more fully described below, with the instant invention, it is also possible to utilize combinations of the biocides even those which ordinarily cannot be admixed in the same solution without adversely affecting the stability or utility thereof.

Further, one or more of the biocides to be employed can be dispersed in one, more or all of the discrete phases contained in the invert emulsion. For example, in the case of an invert emulsion having an external oil system and a multiphase internal aqueous system comprising an oil-in-water emulsion, one or more biocides may be dispersed in: the oil phase of the oil-in-water emulsion, in the water phase of the oil-in-water emulsion, in the external oil system, and/or in any combination or all of said discrete phases of the invert emulsion. Also, the biocides may be of the same type or may be of different types with regard to such characteristics as mode of action (systemic or contact), pest to be controlled (herbicides, insecticides, fungicides, and the like), physical state (wettable powders, liquids).

In accordance with the present invention, the invert emulsions used are preferably those disclosed in Pat. No. 3,479,176 and they are prepared as disclosed therein. Such invert emulsions are prepared using an emulsifiable concentrate available under the trademarks BIVERT, BIVERT-C, and BIVERT-S which consist of petroleum distillate and fatty amine salts and fatty acids. Most suitably, the fatty amine salts and fatty acids comprise from about 6 to about 7 percent by weight of such concentrates with the remainder being the petroleum distillate.

The invert emulsion is formed by mixing the BIVERT with water; it being understood that the biocide, as noted above, can be added to the water and/or the BIVERT before the emulsion is formed. The particular placement of the biocide will depend mainly upon its solubility and, if two or more biocides are to be used, their solubilities and effect on each other.

The amount of BIVERT and water used to make the invert emulsion can vary widely, but most suitable from about 2 to 8 parts by volume water for each part by volume of BIVERT.

After this invert emulsion is formed, it is suspended in an aqueous phase, water, to form the final composition. This is accomplished by thoroughly agitating the invert emulsion and water to thoroughly disperse the invert emulsion throughout the water as small, substantially uniform droplets of water and chemical surrounded by the oil system. This suspended emulsion is stable and maintains the small droplet size. The droplet size can be varied dependent mainly upon the degree of agitation, with a droplet size of from about 50 to 200 microns in diameter being most desired for spray applications. If, upon standing for prolonged periods, the emulsions lose their substantially uniform dispersion in the aqueous phase, they do not lose their small droplet size and can be readily uniformly redispersed with mild agitation. The ability to have a varied and uniform droplet size permits the formation of compositions having the most suitable characteristics for the particular use desired. Table I below shows the droplet size and number per unit volume to give a guide as to spray application and Table II shows the influence of droplet size and wind velocity on droplet movement:

TABLE I

| Droplet Diameter in Microns | | Type of Droplet | No. of droplets per sq. inch from 1 gal. solution distributed uniformly over an acre |
|---|---|---|---|
| 5 | | Fog | 9,000,000 |
| 25 | | | 80,625 |
| 50 | | | 9,224 |
| 100 | | Mist | 1,164 |
| 200 | | | 144 |
| 300 | | | 43 |
| 400 | | | 18 |
| 500 | (1/50") | Light Rain | 9.2 |
| 600 | | | 5.3 |
| 700 | | | 3.3 |
| 800 | | | 2.3 |
| 900 | | | 1.6 |
| 1000 | (1/25") | Moderate Rain | 1.2 |

TABLE II

| Droplet Size Microns | Distance Droplets Move in Winds of | | | | |
|---|---|---|---|---|---|
| | 2 mph | 4mph | 6mph | 8mph | 10 mph |
| 5 | 1⅛ Mi. | 1¼ Mi. | 3⅜ Mi. | 4½Mi. | 11¼ Mi. |
| 10 | 1,490 Ft. | 2,980 Ft. | 4,470 Ft. | 5,960 Ft. | 7,450 Ft. |
| 50 | 59.6 Ft. | 119.2 Ft. | 178.8 Ft. | 238.4 Ft. | 298.0 Ft. |
| 100 | 14.9 Ft. | 29.8 Ft. | 44.7 Ft. | 59.6 Ft. | 74.5 Ft. |
| 200 | 3.7 Ft. | 7.4 Ft. | 11.1 Ft. | 14.8 Ft. | 18.5 Ft. |

Conditions:
1. Drop height--5 Ft.
2. Horizontal air movement--no thermals.
3. Droplet stays same size--no evaporation.

Smaller droplets not only drift farther, but they are also more likely to evaporate and be lost before reaching the locus of the pest infestation.

The amount of water in the aqueous phase must be at least 2 parts by volume for each part by volume of the invert emulsion and the total amount added can be that to give whatever volume desired. In practice, the amount added is that required to bring the batch to the desired size for spraying a given area. In actual operation, it is preferred to continue agitation of the entire batch as it is being used and until spraying is completed in order to be certain that a uniform suspension is maintained.

The invention will be further described in connection with the following examples which are set forth for purposes of illustration only.

EXAMPLE 1

One quart of TREFLAN is mixed in 2 quarts water and then 1 pint BIVERT-S added and mixed to form the invert emulsion. Three gallons of water are then added and the entire composition agitated. Water has been and can be added to make whatever volume is desired (10 gallons or 100 gallons) and the suspension remains stable and uniform.

EXAMPLE 2

One quart TREFLAN is mixed with 1 pint BIVERT-S, two quarts of water added, and the invert emulsion formed by mixing. Then 4 gallons of water are added and agitated to form the composition.

EXAMPLE 3

Mix 2 pounds MILOGARD in 2 quarts water, add 1 pint BIVERT-S and mix. Add 4 gallons of water and agitate.

EXAMPLE 4

Mix ½ pint PARAQUAT in 1 quart water, add ½ pint BIVERT-C and mix. Add water to 3 gallons and agitate.

EXAMPLE 5

Mix 1 pint DEF and 1 pint GUTHION in 1 quart water, add ½ pint BIVERT-C and mix. Add water to make 3 gallons and agitate.

EXAMPLE 6

Mix 1 quart (1 pound) METHYL PARATHION and ¼ pint CHLORDIMEFORM AND ⅛ pound DIPEL with 1 quart water. Add ½ pint BIVERT-C and mix. Stop mixing, add water to bring volume to 2 gallons or larger volume if desired.

EXAMPLE 7

Mix 1 pint METHYL PARATHION with 1 quart water, add ½ pint BIVERT-C, blend by mixing. Then add water to bring volume to 1 gallon and agitate. Additional water can be added to whatever volume is desired.

EXAMPLE 8

Mix 2 pints SUTAN with 2 quarts urea 32% (nitrogen solution), add 1 pint BIVERT-S, mix, add 2 pounds AATREX and mix again. Add 32% aqueous nitrogen solution to make 50 gallons. Agitate and apply on one acre.

EXAMPLE 9

Mix 1 quart TREFLAN with 1 pint BIVERT-S. Add this to 30 gallons of 10-34-0, a liquid fertilizer, agitate and spray on one acre. The amount of 10-34-0, used can vary according to amount of fertilizer desired per acre.

EXAMPLE 10

To 1 quart water, add 1 pound KOCIDE 101, 1 pint BAYFOLAND, 6 ounces AGRI-STREP (fungicides and biocides) and 1 pint GUTHION plus 1½ pints NUDRIN (insecticide). Add ½ pint BIVERT-C and blend. Add water to make 5 gallons. Agitate, spray on one acre.

EXAMPLE 11

Add 2 pounds MANZATE 200 and 1 pound BENLATE to 3 quarts water and mix. Then add ½ pint BIVERT-C and mix. Add water to desired volume to be applied. Agitate and spray on one acre.

EXAMPLE 12

One quart 2,4–D AMINE mixed in 1 quart water, add ½ pint BIVERT-C, mix. Add water to desired volume. Agitate and spray on one acre.

In all of the foregoing twelve examples, stable suspensions of the invert emulsions in the aqueous phase are formed, which emulsions have a substantially uniform particle size and a viscosity similar to water.

EXAMPLE 13

A comparison was made utilizing a spray composition of the present invention and a conventional spray. Both were applied as aerial sprays and contained the identical amounts of biocides. (.75 pounds TOXAPHENE, 0.875 pounds METHYL PARATHION, and 0.133 FUNDAL.)

They were applied to cotton and, after spraying the amount of chemical applied and retained (in p.p.m. METHYL PARATHION) was determined. The results are set forth in Table III.

TABLE III

|  | BIVERTED P.P.M. METHYL PARATHION | CONVENTIONAL P.P.M. METHYL PARATHION |
|---|---|---|
| Immediate | 67.0 | 44.0 |
| 24 Hours | 11.0 | 5.8 |
| 48 Hours | 8.2 | 3.7 |

While the invention has been described in connection with the preferred embodiments, it is not intended to limit the invention to the particular forms set forth, but, on the contrary, it is intended to cover such alternatives, modifications, and equivalents as may be included within the spirit and scope of the invention as defined by the appended claims.

What is claimed is:

1. A pest control composition comprising water having suspended therein substantially uniform droplets of from about 50 to 200 microns in diameter of an invert emulsion comprising an external oil system, an internal system comprising water or an oil-in-water emulsion, and at least one pest control agent present in an amount sufficient to control pests, said agent being contained in at least one of said external or internal systems.

2. The composition of claim 1 wherein the internal system is water.

3. The composition of claim 2 wherein a pest control agent is contained in each of said external and internal systems.

4. The composition of claim 1 wherein the internal system is an oil-in-water emulsion.

5. The composition of claim 4 wherein a pest control agent is contained in each of said external and internal systems.

6. The composition of claim 5 wherein a pest control agent is contained in each of the oil and water of said oil-in-water emulsion.

7. A method for controlling pests comprising applying to the locus of pest infestation a pest control composition comprising water having suspended therein substantially uniform droplets of from about 50 to 200 microns in diameter of an invert emulsion comprising an external oil system, an internal system comprising water or an oil-in-water emulsion, and at least one pest control agent present in an amount sufficient to control pests, said agent being contained in at least one of said external or internal systems.

8. The method of claim 7 wherein the internal system is water.

9. The method of claim 8 wherein a pest control agent is contained in each of said external and internal systems.

10. The method of claim 7 wherein the internal system is an oil-in-water emulsion.

11. The method of claim 10 wherein a pest control agent is contained in each of said external and internal systems.

12. The method of claim 11 wherein a pest control agent is contained in each of the oil and water of said oil-in-water emulsion.

* * * * *